United States Patent [19]

Ichioka et al.

[11] Patent Number: 6,040,490
[45] Date of Patent: *Mar. 21, 2000

[54] PROCESS FOR PRODUCING AROMATIC COMPOUNDS BY DEALKYLATION, TRANSALKYLATION, OR DISPROPORTIONATION

[75] Inventors: Ryoji Ichioka; Shinobu Yamakawa, both of Aichi; Hirohito Okino, Shiga; Hajime Kato; Kazuyoshi Iwayama, both of Aichi; Hiroshi Konta, Mie; Akira Kitamura, Aichi, all of Japan

[73] Assignee: Toray Industries, Inc., Japan

[*] Notice: This patent is subject to a terminal disclaimer.

[21] Appl. No.: 09/132,654

[22] Filed: Aug. 12, 1998

Related U.S. Application Data

[63] Continuation-in-part of application No. 08/955,870, Oct. 22, 1997, Pat. No. 5,847,256, which is a continuation of application No. 08/608,187, Feb. 28, 1996, abandoned.

[30] Foreign Application Priority Data

Mar. 6, 1995 [JP] Japan .................. 7-74587

[51] Int. Cl.[7] .................. C07C 5/22; C07C 4/12; C07C 2/66

[52] U.S. Cl. .................. 585/475; 585/457; 585/470; 585/483; 585/486; 585/488

[58] Field of Search .................. 585/470, 475, 585/483, 486, 457, 488

[56] References Cited

U.S. PATENT DOCUMENTS 5,847,256  12/1998  Ichioka et al. .................. 585/470

FOREIGN PATENT DOCUMENTS

| 939389 | 1/1974 | Canada . |
| A-20 05 820 | 9/1970 | Germany . |
| A-55 164 631 | 12/1980 | Japan . |

*Primary Examiner*—Glenn Caldarola
*Assistant Examiner*—In Suk Bullock
*Attorney, Agent, or Firm*—Austin R. Miller

[57] ABSTRACT

Aromatic hydrocarbons are efficiently converted by bringing feedstock containing from 5 to 50% by weight of an aromatic hydrocarbon having an ethyl group and a $C_9$ alkyl aromatic hydrocarbon into contact with a catalyst capable of disproportionation, trans-alkylation and dealkylation, a secondary particle diameter of a zeolite in the catalyst being 10 μm or less.

14 Claims, 3 Drawing Sheets

PROCESS FOR PRODUCING AROMATIC COMPOUNDS BY DEALKYLATION, TRANSALKYLATION, OR DISPROPORTIONATION

This is a continuation-in-part of application Ser. No. 08/955,870, filed Oct. 22, 1997, now U.S. Pat. No. 5,847, 256, which is a continuation of application Ser. No. 08/608, 187, filed Feb. 28, 1996, now abandoned.

FIELD OF THE INVENTION

The present invention relates to a process for efficient production of xylene or toluene from feedstock containing $C_9$ alkyl aromatic hydrocarbons which are generally regarded as useless by conversion of aromatic hydrocarbons, such as disproportionation, trans-alkylation or dealkylation, this process being carried out in the presence of a specific aromatic hydrocarbon whose concentration is within a certain range and by bringing the feedstock into contact with a catalyst for conversion of an aromatic compound in which a secondary particle diameter of a zeolite is 10 μm or less.

BACKGROUND OF THE INVENTION

A disproportionation reaction and/or a trans-alkylation reaction of aromatic hydrocarbons in production of benzene and xylene by disproportionation of toluene, production of xylene by trans-alkylation of toluene and trimethylbenzene or the like is an industrially important reaction, and a large number of catalyst systems have been so far proposed. In recent years, crystalline aluminosilicate zeolites such as faujasite and mordenite have been found to be effective catalysts. Especially, mordenite has a high disproportionation activity or trans-alkylation activity of aromatic hydrocarbons.

However, U.S. Pat. No. 3,729,521 discloses that mordenite alone is not satisfactory with respect to an activity and a catalytic life and a combination of mordenite with metals belonging to the VIB Group, such as chromium, molybdenum and tungsten or metals belonging to the VIII Group, such as iron, cobalt, nickel and platinum is used to improve the activity and the catalytic life. Further, Japanese Patent Publication No. 45,849/1987 discloses a catalyst composed substantially of a mordenite component and a rhenium component. Nevertheless, this catalyst does not exhibit a satisfactory catalytic activity in a disproportionation reaction and/or a trans-alkylation reaction by which to produce xylene from feedstock containing aromatic hydrocarbons.

Further, there is a process for industrially producing xylene from $C_9$ aromatic hydrocarbons as feedstock with the aid of an amorphous silica-alumina catalyst (PETROTECH, 2(12) 1160, 1970). This process is problematic in that the catalyst has to be continuously regenerated using a moving bed because the yield and the activity are notably decreased over the course of time.

A trans-alkylation reaction of feedstock containing $C_9$ alkyl aromatic hydrocarbons with the aid of a zeolite catalyst has been reported [I. Wang, T. -C. et al., Ind. Chem. Res. 29 (1990) 2005]. However, the yield of xylene formed is not necessarily high. There has been so far no efficient process for producing xylene from $C_9$ aromatic hydrocarbons.

SUMMARY OF THE INVENTION

It is an object of the present invention to provide a process for efficiently producing aromatic compounds such as xylene and toluene by disproportionation, trans-alkylation or dealkylation even from feedstock composed mainly of $C_9$ aromatic hydrocarbons which are generally regarded as useless.

For example, there is a method for efficiently producing xylene in which feedstock containing toluene is subjected to a disproportionation reaction and/or a trans-alkylation reaction. In this method, an ability of producing xylene varies depending on a catalyst used, and a catalyst having a better activity has been therefore in demand. Meanwhile, $C_9$ allyl aromatic hydrocarbons have a less industrial value, and are therefore used as a fuel in many cases. It is possible that ethyltoluene contained in $C_9$ alkyl aromatic hydrocarbons is converted to toluene by a dealkylation reaction and this toluene is formed into industrially useful xylene by a disproportionation reaction using two toluene molecules or a trans-alkylation reaction of toluene and trimethylbenzene. The prior technique involved a problem that ethyltoluene cannot efficiently be dealkylated to form toluene so that the yield of desired xylene is low. The present inventors provide a process for conversion of aromatic hydrocarbons in which aromatic hydrocarbons such as xylene and toluene are efficiently produced from feedstock containing $C_9$ alkyl aromatic hydrocarbons by effective dealkylation of an ethyl group of an ethyl group-containing aromatic hydrocarbon contained therein and a disproportionation reaction and or/a trans-alkylation reaction.

The present inventors have found that xylene or toluene is produced from feedstock containing $C_9$ aromatic hydrocarbons by disproportionation, trans-alkylation or dealkylation, wherein an aromatic hydrocarbon having an ethyl group is present in a fixed amount, and the feedstock is brought into contact with a catalyst containing a zeolite in which a secondary particle diameter of the zeolite is small. The secondary particles of the zeolite refer to particles obtained by agglomerating primary crystals of the zeolite. The secondary particle diameter of the zeolite in the catalyst can easily be examined using a scanning electron microscope (SEM). In the object of the present invention, the secondary particle diameter of the zeolite in the catalyst is 10 μm or less, preferably 5 μm or less. That the secondary particle diameter is 10 μm or less or 5 μm or less can be identified by a method in which a certain portion of a catalyst composition is photographed with SEM and it is confirmed that in the resulting photo, there are no secondary particles having a secondary particle diameter in excess of 10 μm or 5 μm.

That is, the present invention relates to a process for producing xylene or toluene from feedstock containing $C_9$ alkyl aromatic hydrocarbons by conversion of aromatic hydrocarbons such as disproportionation, trans-alkylation or dealkylation, wherein an aromatic hydrocarbon having an ethyl group is present in an amount of from 5 to 50% by weight and the feedstock is brought into contact with a catalyst for a conversion reaction of an aromatic compound in which a secondary particle diameter of a zeolite in the catalyst is 10 μm or less.

DETAILED DESCRIPTION OF THE INVENTION

Figure 1:
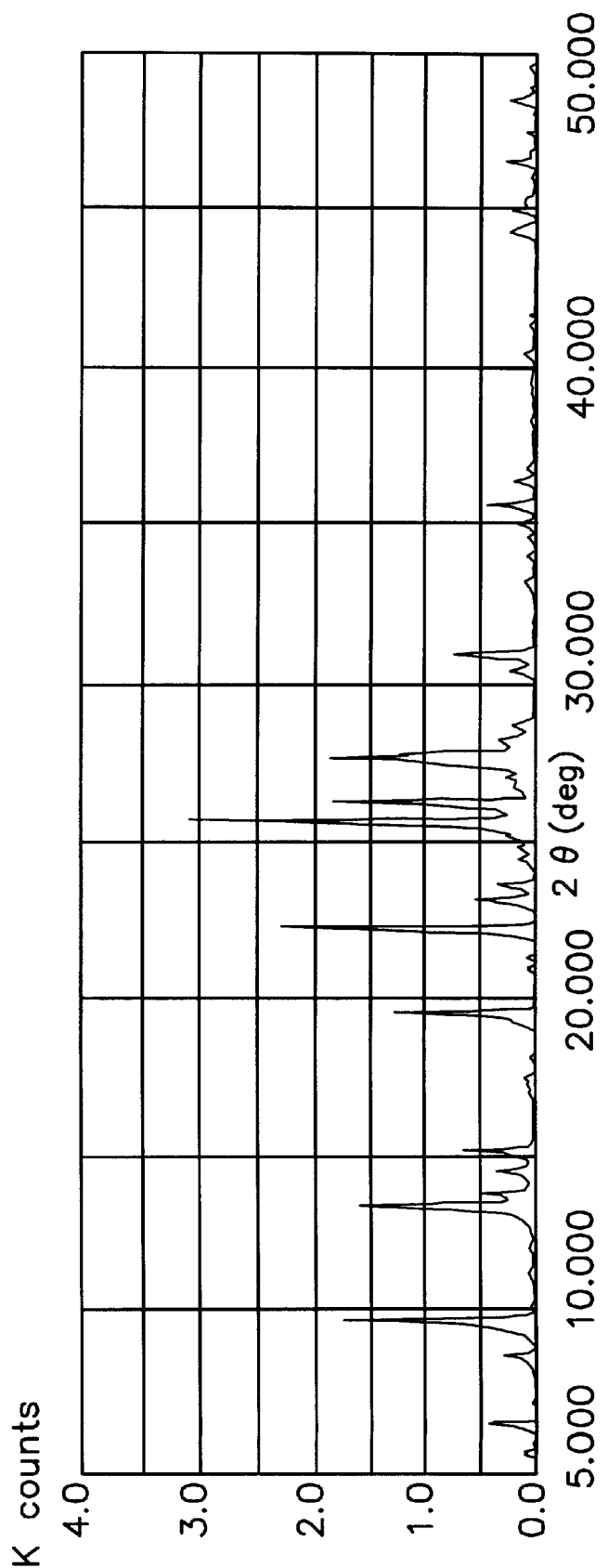
FIG. 1 is an X-ray diffraction pattern of a mordenite-type zeolite formed in Examples.
Figure 2:
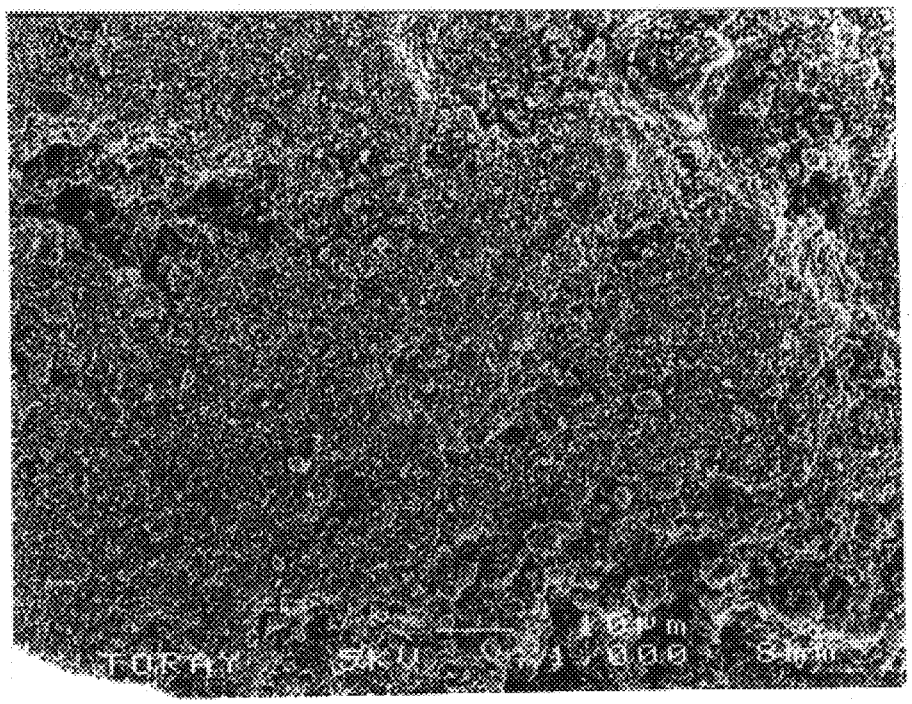
FIG. 2 is an SEM photo of Catalyst A prepared in Examples.
Figure 3:
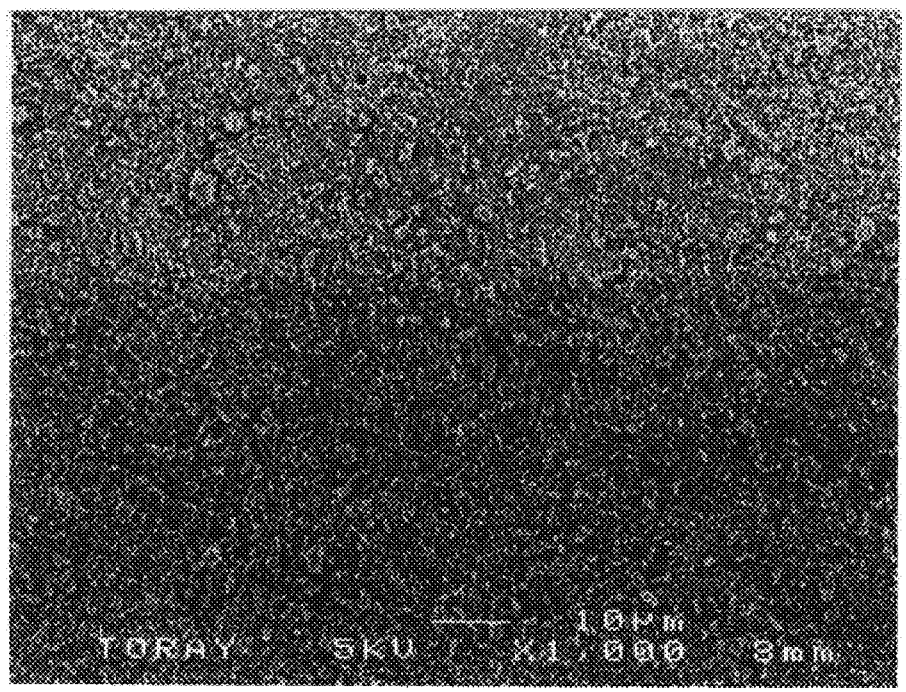
FIG. 3 is an SEM photo of Catalyst B prepared in Examples.
Figure 4:
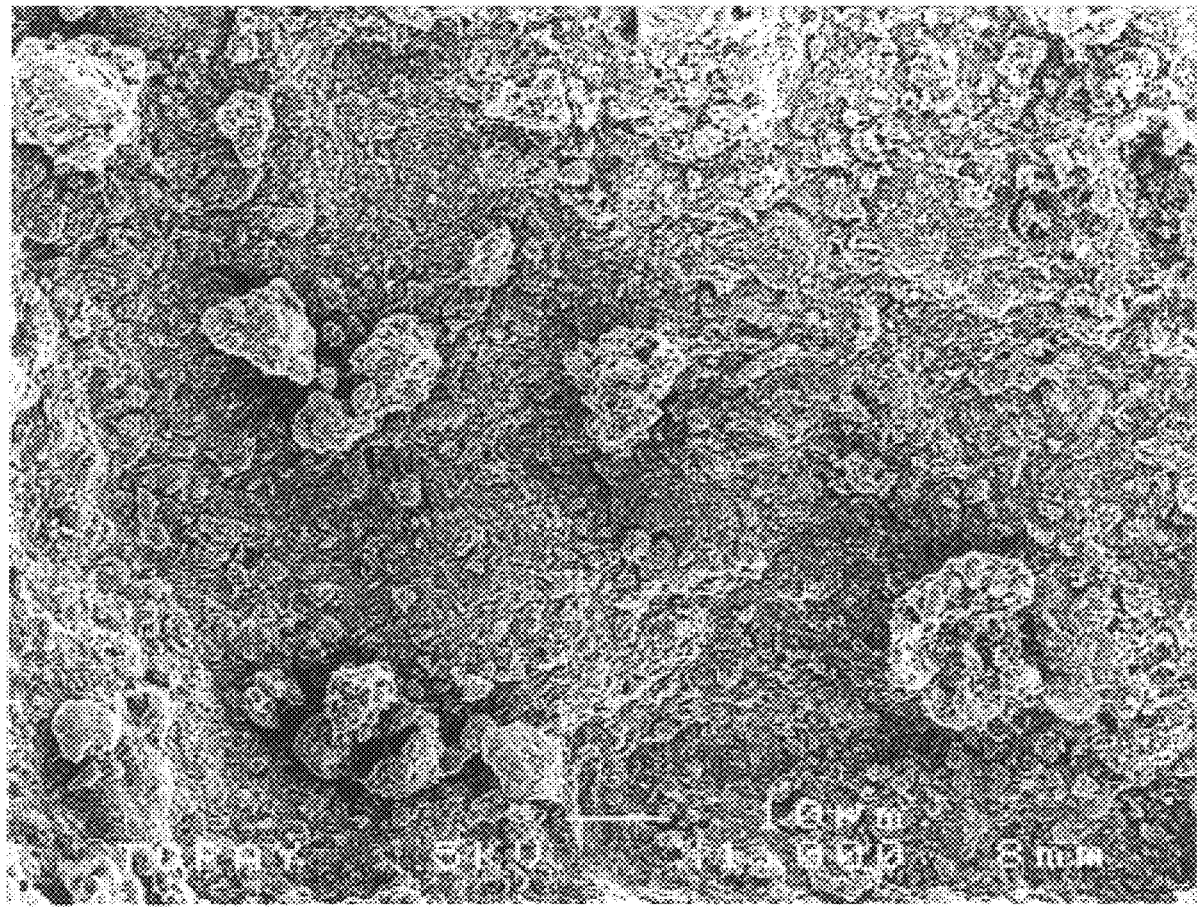
FIG. 4 is an SEM photo of Catalyst C prepared in Examples.

In the present invention, feedstock is composed mainly of $C_9$ alkyl aromatic hydrocarbons. As the aromatic hydrocarbon having the ethyl group, for example, ethylbenzene, methylethylbenzene, dimethylethylbenzene and diethylbenzene are mentioned.

In the feedstock composed mainly of $C_9$ alkyl aromatic hydrocarbons, the aromatic hydrocarbon having the ethyl group is present in an amount of from 5 to 50% by weight, preferably from 8 to 50% by weight, more preferably from 10 to 50% by weight, further preferably from 15 to 50% by weight, making it possible to efficiently produce aromatic hydrocarbons such as xylene and toluene. It is also possible to use feedstock obtained by mixing $C_9$ allyl aromatic hydrocarbons with toluene. The mixing ratio of toluene to $C_9$ alkyl aromatic hydrocarbon is not particularly limited. However, a toluene to $C_9$ alkyl aromatic hydrocarbon ratio (by weight) is preferably between 0 and 1 from the standpoint of the yield of xylene. Further, feedstock may contain benzene. Still further, feedstock may contain, other than the above-mentioned aromatic compound, non-aromatic hydrocarbons such as paraffins and naphthene.

A catalyst is one containing a zeolite and capable of disproportionation, trans-alkylation and dealkylation.

When starting zeolite contained in the catalyst is uniformly mixed with an inorganic oxide and/or a clay and the mixture is molded, the secondary particles are partially collapsed and dispersed. However, when the secondary particles of the zeolite in the catalyst are small enough and highly dispersed, the interaction with the metal component in the catalyst is improved, and a higher yield of xylene is achieved. The secondary particle diameter of the zeolite in the catalyst is controlled by the conditions of forming a catalyst, the secondary particle diameter of the starting zeolite powder and the like. The time of kneading a zeolite with an inorganic oxide and/or a clay and a water content are important as conditions of forming the catalyst. For example, the longer the kneading time, the smaller the secondary particle diameter of the zeolite in the catalyst. Thus, it is desirous. Further, the secondary particle diameter of the starting zeolite powder can be controlled by the composition ratio of the reaction mixture, the crystallization time, the stirring conditions and the drying method, and varies depending on the type of the feedstock used. Therefore, these conditions have to be selected as required. According to the past knowledge, when the alkalinity of the reaction mixture in the formation of a zeolite is decreased or the crystallization time is shortened, the secondary particle diameter tends to decrease. As a zeolite, mordenite is preferable.

In order to efficiently produce aromatic compounds such as xylene and toluene from feedstock containing aromatic hydrocarbons, above all, in order to obtain a high yield of xylene, a catalyst containing hydrogen-type mordenite, an inorganic oxide and/or a clay and rhenium is effective. When feedstock composed of aromatic hydrocarbons contains $C_9$ alkyl aromatic hydrocarbons including ethyltoluene, ethyltoluene is dealkylated into toluene and ethylene with hydrogen-type mordenite. However, since the dealkylation reaction undergoes restriction of thermodynamic equilibrium, the conversion of ethyltoluene cannot be increased satisfactorily. An inorganic oxide and/or a clay having supported thereon at least one metal selected from the metals belonging to the VIB, VIIB and VIII Groups is incorporated into a catalyst. Consequently, hydrogen present in the reaction system causes ethylene formed in the dealkylation reaction of ethyltoluene to be hydrogenated into ethane so as to eliminate control of the conversion of ethyltoluene owing to the restriction of the thermodynamic equilibrium, making it possible to achieve a high conversion. Likewise, aromatic hydrocarbons having an ethyl group and a propyl group are highly dealkylated with this catalyst. The aromatic hydrocarbons formed are directly used as products, or as feedstock of disproportionation and/or trans-alkylation. For example, the yield of xylene is improved by disproportionation of toluene formed through the dealkylation reaction and/or toluene in feedstock, and by trans-alkylation of toluene and trimethylbenzene. Toluene may be withdrawn as a product. Further, a high-boiling compound formed by a side reaction undergoes hydrogenolysis on an inorganic oxide and/or a clay having supported thereon at least one metal selected from metals belonging to the VID, VIB and BIII Groups to control coking on a catalyst, to inhibit deactivation of the catalyst and to prolong the catalytic life.

The zeolite used in the present invention is preferably hydrogen-type mordenite. Mordenite having a silica to alumina molar ratio of from 15 to 30 is preferably used. Mordenite having a silica to alumina molar ratio of from 15 to 30 is obtained by a method in which aluminum is removed from mordenite having a low silica to alumina molar ratio through acid extraction or a method in which mordenite having a silica to alumina molar ratio of from 15 to 30 is directly formed. Synthetic mordenite directly formed is preferable. A method of forming mordenite is disclosed in, for example, American Mineralogist, vol. 57 (1972), pp. 1146–1151, and Japanese Patent Publication Nos. 51,969/1988 and 31,006/1990. Hydrogen-type mordenite is usually formed by subjecting mordenite containing a metallic cation directly to ion exchange with an acid or subjecting the same to ion exchange with an aqueous solution containing an ammonium ion to provide ammonium-type mordenite, and drying and baking the same. It is preferable to convert ammonium-type mordenite into hydrogen-type mordenite. The ion exchange may be conducted before forming a zeolite. However, the ion exchange is preferably conducted after forming a zeolite from the industrial standpoint. When mordenite is treated with a carboxyl group-containing organic acid such as lactic acid, malic acid, tartaric acid or citric acid, the catalytic activity is improved. Accordingly, this treatment is conducted as required.

The inorganic oxide and/or the clay is inevitable to highly disperse secondary particles of a zeolite and to disperse and support rhenium. Known examples of the inorganic oxide include alumina, silica-alumina, silica, titania and magnesia. Any of these inorganic oxides are available. Alumina is preferable. As alumina, boehmite, boehmite gel, gibbsite, bialite, nordstrandite, diaspore and amorphous alumina gel are known. Any of these aluminas are available. Boehmite is preferable. It is well known that alumina is formed into γ-, η- or δ-alumina. Aluminas having these forms are also available. As a binder for forming a catalyst, alumina sol and alumina gel are available. These aluminas can effectively be used as those having rhenium supported thereon. The clay is not particularly limited. Examples of the clay include natural clays such as montmorillonite, kaolin, sepiolite and acid clay; and purified clays.

The zeolite should contain at least one metal selected from metals belonging to the VIB, VIIB and VIII Groups in an amount of from 0.001 to 5% by weight, preferably from 0.02 to 1% by weight as element. As the metal, rhenium is especially preferable.

Rhenium can be present in the form of a metal, or in the form of an oxide, a sulfide or a selenide. As a rhenium component, perrhenic acid and ammonium rhenate are especially preferable. A catalyst having supported thereon a rhenium component is formed most preferably by the following method. That is, mordenite and an inorganic oxide and/or a clay are uniformly mixed and molded, and the product is dried and baked. Mordenite is then formed into hydrogen-type or ammonium-type mordenite, and dipped in a rhenium-containing aqueous solution. The catalyst having rhenium supported thereon is then dried and baked. Ammonium-type mordenite is converted into hydrogen-type mordenite during the baking. The baking is preferably conducted in an oxygen-containing atmosphere at from 300 to 650° C.

The catalyst prepared according to the present invention is used in the conversion of aromatic hydrocarbons. Specifically, aromatic hydrocarbons are brought into contact with this catalyst to convert the same into other aromatic hydrocarbons by at least one reaction of disproportionation, trans-alkylation and dealkylation. For example, an intermolecular transfer reaction of a methyl group by disproportionation of toluene, xylene and trimethylbenzene, a trans-alkylation reaction between toluene and trimethylbenzene or tetramethylbenzene, a trans-alkylation reaction between benzene and xylene, trimethylbenzene or tetramethylbenzene, and a dealkylation reaction of an ethyl group or a propyl group of aromatic hydrocarbons having at least one ethyl group or propyl group are mentioned. Preferable is a trans-alkylation reaction of feedstock composed mainly of $C_9$ allyl aromatic hydrocarbons.

In the present invention, any of the aromatic hydrocarbons formed in the reaction may be withdrawn as a product. The aromatic hydrocarbons except product hydrocarbons may be recycled as feedstock, as required. For example, toluene formed may be withdrawn as a product or as feedstock for production of xylene. That is, in the present invention, the most valuable aromatic compounds can be provided as products according to the demand. Further, the composition of feedstock can be selected as required in order to obtain such aromatic compounds. As a product, xylene and toluene are especially preferable. Of these, xylene is more preferable. Still further, a fraction having a specific boiling point in a reaction product can also be used as a gasoline base material.

In the conversion reaction of aromatic hydrocarbons in which the catalyst of the present invention is used, it is indispensable that hydrogen is present in the reaction system. Hydrogen to be fed is preferably used at a hydrogen to aromatic hydrocarbon molar ratio of from 1 to 10. It is preferable that feedstock is brought into contact with the catalyst at a reaction temperature of from 300 to 550° C. and a reaction pressure of from 1 to 6 MPa-G with WHSV (weight hourly space velocity) of from 0.5 to 10/$h^{-1}$.

The present invention will be described specifically by referring to the following Examples.

EXAMPLE 1

Synthesis of a mordenite-type zeolite:

Solid sodium hydroxide (21.3 g, containing 96.0% by weight of NaOH and 4.0% by weight of $H_2O$, Katayama Kagaku) and 21.3 g of a tartaric acid powder (containing 99.7% by weight of tartaric acid and 0.3% by weight of $H_2O$, Katayama Kagaku) were dissolved in 586.8 g of water. To this solution were added 29.2 g of a sodium aluminate solution (containing 18.5% by weight of $Al_2O_3$, 26.1% by weight of NaOH and 55.4% by weight of $H_2O$, Sumitomo Chemical) to form a uniform solution. To this mixed solution were gradually added 111.5 g of a silicic acid powder (containing 91.6% by weight of $SiO_2$, 0.33% by weight of $Al_2O_3$ and 0.27% by weight of NaOH, Nip Seal VN-3, Nippon Silica) while being stirred to prepare a uniform slurry aqueous reaction mixture. This reaction mixture had the following composition ratio (molar ratio).

| | |
|---|---|
| $SiO_2/Al_2O_3$ | 30 |
| $H_2O/SiO_2$ | 20 |
| $OH^-/SiO_2$ | 0.25 |
| $A/Al_2O_3$ | 2.5 |
| | (A : tartrate) |

The reaction mixture was charged into a 1,000-milliliter autoclave, and the autoclave was sealed. The reaction mixture was then reacted at 160° C. for 72 hours while being stirred at 250 rpm.

After the completion of the reaction, the reaction product was washed with distilled water and filtered 5 times, and the resulting product was dried overnight at approximately 120° C. The thus-obtained product was a mordenite-type zeolite having an X-ray diffraction pattern shown in FIG. 1. The composition of this zeolite was analyzed. As a result, it had the following composition ratio (molar ratio) in the anhydrous state.

$1.02Na_2O.Al_2O_3.18.6SiO_2$

Production of a catalyst:

A pasty mixture was prepared by mixing 74.6 g of the mordenite powder (containing 93.8% by weight of mordenite) prepared by the above-mentioned method, 39.5 g of an alumina powder (containing 76.1% by weight of $Al_2O_3$, SCF type, Condia) having a boehmite structure (α-alumina monohydrate), 80 g of alumina sol (containing 10% by weight of $Al_2O_3$, Colloidal Alumina 200, Nissan Chemical), 10 g of alumina gel powder (containing 70% by weight of $Al_2O_3$, Cataloid AP (C-10), Shokubai Kagaku) and 10 g of distilled water. After kneading for approximately 1 hour, the pasty mixture was molded into cylindrical pellets each having an outer diameter of 1.2 mm and a length of 1.0 mm. The pellets were then dried overnight at 120° C. The dried pellets (15 g in absolute dry condition) were baked in an atmosphere of air at 400° C. for 2 hours, and cooled in a desiccator. The cooled pellets were treated at from 80 to 85° C. for 1 hour using 30 ml of a 10% by weight ammonium chloride aqueous solution. The treated pellets were strained off the solution, and treated likewise with the addition of 30 ml of an ammonium chloride aqueous solution. This procedure was repeated 4 times. Subsequently, the thus-treated pellets were strained off the solution. The resulting pellets were then washed with distilled water 5 times, treated at from 80 to 85° C. for 4 hours using 30 ml of an aqueous solution containing 5% by weight of tartaric acid, strained off the solution, and washed with distilled water 5 times. Further, the pellets were dipped in 21 g of water containing 0.039 g of rhenium oxide (VII) (Re 207) for 4 hours for impregnation with rhenium. The thus-treated pellets were strained off the solution, then dried overnight at 120° C., and baked in an atmosphere of air at 540° C. for 2 hours to obtain Catalyst A. The SEM observation of this catalyst revealed that the maximum secondary particle diameter of mordenite in the catalyst was 7 μm.

EXAMPLE 2

Catalyst B was prepared in the same manner as in Example 1 except that the kneading time in the molding of the catalyst was approximately 5 hours. The SEM observation of this catalyst revealed that the maximum secondary particle diameter of mordenite in the catalyst was 3 μm.

COMPARATIVE EXAMPLE 1

Catalyst C was prepared in the same manner as in Example 1 except that the kneading time in the molding of the catalyst was approximately 20 minutes. The SEM observation of this catalyst revealed that the maximum secondary particle diameter of mordenite in the catalyst was 20 μm.

EXAMPLE 3

With respect to Catalysts A to C having the above-mentioned varied secondary particle diameters of mordenite, the catalytic activity in the trans-alkylation reaction of alkyl aromatic hydrocarbons including ethyltoluene was measured using a fixed-bed catalytic reactor. The results are shown in Table 1. From Table 1, it becomes apparent that the smaller the maximum value of the secondary particle diameter of mordenite in the catalyst, the higher the disproportionation, trans-alkylation or dealkylation activity, and the catalyst gives a large amount of xylene. The secondary particle diameter of mordenite in the catalyst has to be at most 10 μm.

Feedstock composition ratio:
ethyltoluene/(trimethylbenzene+ethyltoluene) ratio: 35% by weight Reaction conditions:
Temperature: 400° C.
Pressure: 3 MPa-G
WHSV: 2.5 h$^{-1}$
H$_2$/feedstock: 4.0 mols/mol

TABLE 1

| Catalyst | Maximum secondary particle diameter (μm) of mordenite in catalyst | Conversion of ethyltoluene (wt. %) | Amount (g) of xylene produced per 100 g of feedstock |
|---|---|---|---|
| A | 7 | 95.5 | 31.6 |
| B | 3 | 96.8 | 31.8 |
| C | 20 | 78.9 | 25.1 |

EXAMPLE 4

A pasty mixture was prepared by mixing the mordenite powder (105 g, containing 93.8% by weight of mordenite) prepared by the method in Example 1, 45 g of an alumina powder (containing 76.1% by weight of Al$_2$O$_3$, SCF type, Condia) having a boehmite structure (α-alumina monohydrate), 12 g of alumina sol (containing 10% by weight of Al$_2$O$_3$, Colloidal Alumina 200, Nissan Chemical), 10.5 g of an alumina gel powder (containing 70% by weight of Al$_2$O$_3$, Cataloid AP (C-10), Shokubai Kagaku) and 10 g of distilled water. After kneading for approximately 2 hours, the pasty mixture was molded into cylindrical pellets each having an outer diameter of 1.2 mm and a length of 1.0 mm. The pellets were then dried overnight at 120° C. The dried pellets (15 g in absolute dry condition) were baked in an atmosphere of air at 400° C. for 2 hours, and cooled in a desiccator. The cooled pellets were treated at from 80 to 85° C. for 1 hour using 100 ml of a 10% by weight ammonium chloride aqueous solution. The treated pellets were then strained off the solution, and treated likewise with the addition of 100 ml of an ammonium chloride aqueous solution. This procedure was repeated 4 times. Subsequently, the thus-treated pellets were strained off the solution. The resulting pellets were then washed with distilled water 5 times, treated at from 80 to 85° C. for 3 hours using 100 ml of a 5% by weight tartaric acid aqueous solution, strained off the solution, and washed with distilled water 5 times. Further, the pellets were dipped in 6.5 g of water containing 0.325 g of rhenium oxide (VII) (Re 207) for 4 hours for impregnation with rhenium. The thus-treated pellets were strained off the solution, then dried overnight at 120° C., and baked in an atmosphere of air at 540° C. for 2 hours to obtain Catalyst D. Catalyst D contained 0.25% by weight of rhenium in absolute dry condition.

Feedstock composed of trimethylbenzene (TMB for short) as a C$_9$ alkyl aromatic hydrocarbon and methylethylbenzene (ET for short) as an aromatic hydrocarbon having an ethyl group in varied ratios was brought into contact with Catalyst D, and the reaction was conducted in a fixed-bed catalytic reactor. The results are shown in Table 2. As is apparent from Table 2, the presence of ET increases the amount of xylene formed, and when the ET concentration in the feedstock exceeds 50% by weight, the amount of xylene formed is decreased.

The reaction conditions are as follows.
Temperature: 400° C.
Pressure: 4 MPa-G
WHSV: 2.5 h$^{-1}$
H$_2$/feedstock: 4.0 mol/mol

TABLE 2

| Run No. | Ratio (by weight) of ET/(TMB + ET) in feedstock | Amount (g) of xylene produced per 100 g of feedstock |
|---|---|---|
| 1 | 0 | 20 |
| 2 | 0.25 | 31 |
| 3 | 0.45 | 34 |
| 4 | 0.65 | 28 |

EXAMPLE 5

Feedstock obtained by adding ethylbenzene (EB for short) or diethylbenzene (DEB for short) instead of ET as an aromatic hydrocarbon having an ethyl group to TMB was brought into contact with Catalyst D used in Example 4 in a fixed-bed catalytic reactor.

The amount of xylene produced per 100 g of feedstock is shown in Table 3. From Table 3, it becomes apparent that a considerable amount of xylene can be formed in the reaction of a mixture of TMB with the aromatic hydrocarbons having the ethyl group, other than ET. The reaction conditions are the same as those in Example 4.

TABLE 3

| Run No. | Composition (by weight) of feedstock | Amount (g) of xylene produced per 100 g of feedstock |
|---|---|---|
| 1 | TMB + EB (EB/THB = 30/70) | 34 |
| 2 | THB + DEB (DEB/TMB = 36/65) | 34 |

EXAMPLE 6

Catalysts were prepared in the same manner as in Example 4 except that the amount of rhenium was varied.

Using the catalysts in a fixed-bed catalytic reactor, xylene was produced in the same manner as in Example 4 from the same feedstock as used in Run No. 3 in Example 1. The amount of xylene produced per 100 g of feedstock was measured under the same conditions as in Example 4. The results are shown in Table 4. Table 4 reveals that the amount of xylene increases with the increasing amount of rhenium. The effect of rhenium is outstanding especially in the range of from 0.02% by weight to 0.10% by weight, and levels off beyond 0.10% by weight.

TABLE 4

| Run No. | Content of rhenium as element (wt. %) | Amount (g) of xylene produced per 100 g of feedstock |
| --- | --- | --- |
| 1 | 0 | 20 |
| 2 | 0.01 | 23 |
| 3 | 0.02 | 32 |
| 4 | 0.10 | 34 |
| 5 | 0.20 | 34 |

EXAMPLE 7

Catalysts containing rhenium, nickel, cobalt, molybdenum, chromium and tungsten were prepared according to the recipe shown in Table 5. With respect to the catalysts containing rhenium, nickel, cobalt and molybdenum, Example 4 was repeated except that 50 g (in absolute dry condition) of the catalyst was dipped in each solution of a compound shown in Table 5, dried at 120° C. for 16 hours, and baked at 540° C. for 8 hours. With respect to the catalysts containing chromium and tungsten, Example 4 was repeated except that a compound shown in Table 5 was mixed in the kneading. In this manner, Catalysts E to J containing rhenium, nickel, cobalt, molybdenum, chromium and tungsten were obtained.

TABLE 5

| Catalyst | Metal | Compound | Incorporated by |
| --- | --- | --- | --- |
| E | Re | $Re_2O_7$ | Dipping and impregnation |
| F | Ni | $Ni(NO_3)_2 6H_2O$ | Dipping and impregnation |
| G | Co | $CO(NO_3)_2 6H_2O$ | Dipping and impregnation |
| H | Mo | $(NH_4)_6Mo_7G_4H_2O$ | Dipping and impregnation |
| I | Cr | $CrO_3$ | Mixing |
| J | W | $WO_3$ | Mixing |

Using each of Catalysts E to J in a fixed-bed catalytic reactor, xylene was produced under the same conditions as in Example 4 from the same feedstock as used in Run No. 3 in Example 4. The results are shown in Table 6. Table 6 reveals that the catalyst containing rhenium is most active with the minimal content.

TABLE 6

| Catalyst | Metal | Content (wt. %) of metal (as element) in catalyst | Amount (g) of xylene produced from 100 g of feedstock |
| --- | --- | --- | --- |
| E | Re | 0.15 | 34 |
| F | Ni | 0.40 | 30 |
| G | Co | 0.40 | 26 |
| H | Mo | 0.40 | 32 |
| I | Cr | 0.40 | 28 |
| J | W | 0.24 | 22 |

EXAMPLE 8

Three catalysts, each containing a different amount of rhenium, were prepared in the same manner as in Example 4. Using each catalyst in a fixed-bed catalytic reactor, xylene was produced under the same conditions as in Example 4 from the same feedstock as used in Run No. 3 in Example 4. The change in the amount of xylene over the course of time was examined. The rate of decrease (weight %/day) in the yield of xylene in each catalyst is shown in Table 7. Table 7 reveals that the increase in the amount of rhenium is effective for controlling deterioration of the catalyst.

TABLE 7

| Content (wt. %) of rhenium (as element) in catalyst | Decrease in yield of xylene (wt. % per day) |
| --- | --- |
| 0 | 1.50 |
| 0.01 | 0.96 |
| 0.20 | less than 0.04 |

What is claimed is:

1. A process for conversion of aromatic hydrocarbons, which comprises bringing feedstock containing from 5 to 50% by weight of an aromatic hydrocarbon having an ethyl group and a $C_9$ alkyl aromatic hydrocarbon into contact with a catalyst capable of disproportionation, trans-alkylation and dealkylation, in the presence of hydrogen, a secondary particle diameter of a zeolite in the catalyst being 10 μm or less.

2. The process of claim 1, wherein the aromatic hydrocarbon having the ethyl group is contained in an amount of from 8 to 50% by weight.

3. The process of claim 1 or 2, wherein the secondary particle diameter of the zeolite is 5 μm or less.

4. The process of claim 1, wherein the zeolite is mordenite.

5. The process of claim 1, wherein the catalyst contains mordenite, an inorganic oxide and/or clay and at least one metal selected from metals belonging to the VIB, VIIB and VIII Groups.

6. The process of claim 5, wherein at least one metal selected from metals belonging to the VIB, VIIB and VIII Groups is rhenium.

7. The process of claim 6, wherein the amount of rhenium is between 0.001 and 5% by weight as element.

8. The process of claim 6, wherein the amount of rhenium is between 0.02 and 1% by weight as element.

9. The process of claim 1, wherein the zeolite is a hydrogen-type zeolite.

10. The process of claim 4, wherein the silica to alumina molar ratio of mordenite is between 15 and 30.

11. The process of claim 5, wherein the inorganic oxide is at least one type selected from alumina, silica, silica-alumina, titania and magnesia.

12. The process of claim 11, wherein the inorganic oxide is alumina.

13. The process of claim 12, wherein alumina is alumina having a boehmite structure.

14. A process for conversion of aromatic hydrocarbons, which comprises bringing feedstock containing from 5 to 50% by weight of an aromatic hydrocarbon having an ethyl group and a $C_9$ alkyl aromatic hydrocarbon into contact with a catalyst capable of disproportionation, trans-alkylation and dealkylation, a secondary particle diameter of a zeolite in the catalyst being 10 µm or less, wherein the reaction is performed in the presence of hydrogen at a temperature of from 300 to 550° C. and a pressure of from 1 to 6 MPa with WHSV of from 0.5 to 10 $hr^{-1}$ at a hydrogen to aromatic hydrocarbon molar ratio of from 1 to 10.

* * * * *